(12) United States Patent
Kiraly

(10) Patent No.: US 9,465,090 B2
(45) Date of Patent: Oct. 11, 2016

(54) METHOD OF MAGNETIC RESONANCE-BASED TEMPERATURE MAPPING

(75) Inventor: Atilla Peter Kiraly, Plainsboro, NJ (US)

(73) Assignee: Siemens Aktiengesellschaft, München (DE)

(*) Notice: Subject to any disclaimer, the term of this patent is extended or adjusted under 35 U.S.C. 154(b) by 296 days.

(21) Appl. No.: 13/151,523

(22) Filed: Jun. 2, 2011

(65) Prior Publication Data

US 2011/0313278 A1    Dec. 22, 2011

Related U.S. Application Data

(60) Provisional application No. 61/352,881, filed on Jun. 9, 2010.

(51) Int. Cl.
    *G01R 33/48*     (2006.01)
    *A61B 5/01*     (2006.01)
    *A61B 5/055*     (2006.01)
    *G01R 33/563*     (2006.01)

(52) U.S. Cl.
    CPC .......... *G01R 33/4804* (2013.01); *A61B 5/015* (2013.01); *A61B 5/055* (2013.01); *G01R 33/56358* (2013.01)

(58) Field of Classification Search
    CPC .............. G01R 33/4804; G01R 33/56358; A61B 5/055; A61B 5/01; A61B 5/015; A61B 8/485; A61B 2018/00803; G06T 2207/10088; G01N 2203/0094
    USPC .................. 600/412, 410; 382/128
    See application file for complete search history.

(56) References Cited

U.S. PATENT DOCUMENTS

| | | | | |
|---|---|---|---|---|
| 4,914,608 | A * | 4/1990 | LeBihan | G01R 33/4804 324/315 |
| 6,067,371 | A * | 5/2000 | Gouge et al. | 382/128 |
| 2005/0251120 | A1* | 11/2005 | Anderson et al. | 606/20 |
| 2006/0159328 | A1* | 7/2006 | Vaz et al. | 382/131 |
| 2006/0184025 | A1* | 8/2006 | Sumi | A61B 5/0048 600/438 |
| 2008/0097207 | A1* | 4/2008 | Cai | 600/442 |
| 2010/0179414 | A1* | 7/2010 | Kuhn | A61N 7/02 600/411 |

OTHER PUBLICATIONS

Kruse et al., "Tissue characterization using magnetic resonance elastography: preliminary results", Phys. Med. Biol., Jan. 2000, pp. 1579-1590.*

Seeton, "Viscosity-temperature correlation for liquids", Tribology Letters, vol. 22, No. 1, Apr. 2006, pp. 67-78.*

Sinkus et al., "Viscoelastic shear properties of in vivo breast lesions measured by MR elastography", Magnetic Resonance Imaging, 2005, pp. 159-165.*

Le et al., "Feasibility of Simultaneous Temperature and Tissue Stiffness Detection by MRE", Magnetic Resonance in Medicine, 2006, pp. 700-705.*

Plewes et al., "Visualization and quantification of breast cancer biomechanical properties with magnetic resonance elastography", Phys. Med. Biol., vol. 45, Jan. 2000, pp. 1591-1610.*

Le Bihan et al., "Temperature Mapping with MR Imaging of Molecular Diffusion: Application to Hyperthermia", Radiology, vol. 171, 1989, pp. 853-857.*

* cited by examiner

*Primary Examiner* — Katherine Fernandez

(57) ABSTRACT

An MRI method (10) to map the temperature of a bodily tissue using measurements of the tissue density.

3 Claims, 4 Drawing Sheets

| Temperature (°C) | Dynamic Viscosity $\eta$ $(N s/m^2) \times 10^{-3}$ | Kinematic Viscosity $\nu$ $(m^2/s) \times 10^{-4}$ |
| --- | --- | --- |
| 0 | 1.787 | 1.787 |
| 5 | 1.519 | 1.519 |
| 10 | 1.307 | 1.307 |
| 20 | 1.002 | 1.004 |
| 30 | 0.789 | 0.801 |
| 40 | 0.653 | 0.658 |
| 50 | 0.547 | 0.553 |
| 60 | 0.467 | 0.475 |
| 70 | 0.404 | 0.413 |
| 80 | 0.355 | 0.365 |
| 90 | 0.315 | 0.326 |
| 100 | 0.282 | 0.294 |

Figure 2

METHOD OF MAGNETIC RESONANCE-BASED TEMPERATURE MAPPING

CROSS-REFERENCE TO RELATED APPLICATIONS

This application claims the benefit of Provisional U.S. Patent Application Ser. No. 61/352,881, entitled, "Novel Approach to MR Temperature Mapping", filed in the name of Atilla Peter Kiraly on Jun. 9, 2010, the disclosure of which is also hereby incorporated herein by reference.

FIELD OF THE INVENTION

This invention generally relates to magnetic resonance (MR) imaging. More particularly, this invention relates to MR temperature mapping.

BACKGROUND OF THE INVENTION

Magnetic resonance (MR) imaging techniques to provide temperature mapping of anatomical objects, such as tissues, organs, etc. can be useful for several clinical purposes, such as tumor ablation via heating or cooling. For example, real-time knowledge of the temperature of a target tissue (i.e., a tissue under examination) provides feedback to a health professional in determining the correct application of heat or cold, either invasively though a probe or externally through high intensity focused ultrasound (HIFU). Additionally, temperature data of a target tissue may be useful in diagnosing disease in respective patients.

Recently, MR imaging using proton resonance frequency shift has been used to measure real-time temperature changes in tissues. Generally, changes in the temperature of a material result in changes in the proton resonance frequency phase. An MR imaging scanner may be used to measure proton resonance shift of a target tissue and then calculate a change in temperature according to the following:

$$\Delta T = \frac{\Delta \Phi}{\alpha 2\pi \bar{\gamma} B_o TE},$$

where $\Delta T$ is the change in the temperature of the target tissue, $\Delta \phi$ is the change in the magnetic flux of the static magnet of the MR scanner, $B_o$ is the strength of the static magnet of the MR scanner, $\alpha$ is a constant equal to 0.01 ppm/° C., $\gamma$ is the proton resonance frequency of the target tissue, and TE is the transmit echo time of the MR imaging. However, a baseline of the proton resonance frequency phase needs to be established since this approach measures a shift in the proton resonance. Further, there is a need for accompanying methods to account for a baseline drift of MR images over time and to compensate for the drift, for example, by sampling a region of the target tissue that does not have any anticipated temperature changes.

Other MR imaging techniques may also be able to provide MR temperature mapping. For example, MR elastography has recently been developed to measure the stiffness and viscosity of the liver and assist in diagnosing disease in the liver, such as liver fibrosis. Briefly, MR elastography is implemented by coupling an external acoustic transducer to the patient or target anatomical object. An MR scanner is then employed to apply MR imaging to the patient or target anatomical object using a modified phase-contrast gradient-echo imaging sequence. Multiple phase-offset images are obtained during an imaging cycle. The MR scanner processes the images and uses the wavelength visible on the phase-difference images to calculate a shear modulus and, thereby, measure the stiffness and viscosity of the target anatomical object. Health professionals are extending this MR imaging technique to other applications. It would be advantageous to use MR elastography to obtain temperature measurements of an anatomical object as well. This would have the further benefit of allowing additional patient data to be obtained using existing clinical protocols.

SUMMARY OF THE INVENTION

The aforementioned problems are obviated by the present invention which provides a method of taking temperature measurements of an anatomical object, comprising a) obtaining a measurement of viscosity of the anatomical object using MR elastography and b) correlating the viscosity measurement to a temperature. The correlating step may comprise correlating the viscosity measurement based on a model of the anatomical object viscosity at different temperatures. In such case, the correlating step may further comprise correlating the viscosity measurement based on a generalized model of tissue viscosity at different temperatures in the case the target anatomical object comprises a type of tissue. Also, the correlating step may further comprise defining regions of different tissue types, each defined region utilizing a respective model of viscosity at different temperatures.

Alternatively, the correlating step may comprise correlating the viscosity measurement based on a critical point of anatomical object change. The critical point of anatomical object change may comprise a viscosity change indicative of a respective estimated temperature. In such case, the obtaining step may comprise detecting a sudden increase or sudden decrease in viscosity of the anatomical object. Also, the critical point of anatomical object change may comprise either ice formation or protein denaturalization. The obtaining step may then comprise detecting ice formation by analyzing the propagating waves around the regions of the target anatomical object.

The present invention also provides a method of obtaining temperature measurements of a target anatomical object using magnetic resonance (MR) imaging, comprising a) generating acoustic waves that propagate through the target anatomical object; b) acquiring MR images of the target anatomical object using a modified phase-contrast gradient-echo MR imaging sequence; c) obtaining elastography and/or viscosity measurements of the target anatomical object by processing the acquired MR images; and d) relating the elastography and/or viscosity measurements to temperature measurements. The generating step may comprise applying oscillatory shear waves of a given frequency. The generating step may also comprise applying the acoustic waves in pulses having a cycle time that takes into account echo delay of the MR imaging. The acquiring step may comprise acquiring images of the propagation of the acoustic waves through the target anatomical object. In such case, the acquiring step may also comprise acquiring multiple phase-offset MR images during an imaging cycle and processing the acquired MR images may comprise measuring the propagation of the acoustic waves through the target anatomical object at multiple frequencies of the acoustic waves.

The obtaining step may comprise detecting sudden changes in elastography or viscosity of the anatomical object and the relating step may comprise relating a sudden change in elastography or viscosity to a respective estimated temperature. Alternatively, the relating step may comprise referencing a model of the target anatomical object that correlates the elastography and/or viscosity measurements to temperature measurements. In the case of the target anatomical object comprising a type of tissue, the referencing step may comprise referencing a generalized tissue model.

The present invention also provides a system for mapping the temperature of an anatomical object, comprising a wave generator that introduces propagating acoustic waves to the anatomical object; and a magnetic resonance imaging system having an imager that images motion-encoded acoustic waves propagating through the anatomical object to acquire image data and a processor that manipulates the acquired image data to measure the anatomical object viscosity and to obtain a temperature mapping of the anatomical object based on the viscosity measurement. The wave generator may comprise an ultrasonic transducer that is used for high intensity focused ultrasound therapy.

The present invention also provides a method of magnetic resonance-based temperature mapping, comprising determining temperature data of a tissue by magnetic resonance elastography and generating a visualization of a temperature map of the tissue.

BRIEF DESCRIPTION OF THE DRAWINGS

For a better understanding of the present invention, reference is made to the following description of exemplary embodiments thereof, and to the accompanying drawings, wherein:

FIG. 2 is a table showing the values of dynamic viscosity and kinematic viscosity of water at different temperatures;

DETAILED DESCRIPTION

A health professional is often assisted in the diagnosis of disease of an anatomical object (e.g., tissue, organ, etc.) by obtaining morphologic information of the object, such as size, shape, stiffness, etc. In many circumstances, this is accomplished by manual palpation by the health professional. As noted above, MR elastography generally provides a noninvasive, objective measurement or assessment of the viscoelastic properties of anatomical objects, based on the object response to acoustic or sound waves. In effect, MR elastography provides a visual palpation technique.

The present invention provides a method 10 to measure real-time temperature changes of an anatomical object using MR elastography. More particularly, the method 10 uses MR imaging gradient-echo sequences to measure the elastography and/or the viscosity of the anatomical object and, from the viscosity measurements, obtain correlated temperatures of the object. The temperature correlations may be based on a model of the anatomical object viscosity at different temperatures. In this way, the present invention replaces existing MR imaging techniques using proton resonance frequency shift to measure temperature changes. Since the method 10 does not measure a shift, no base-line needs to be taken and the measurements may proceed directly once a specific anatomical object model is known.

Figure 1:
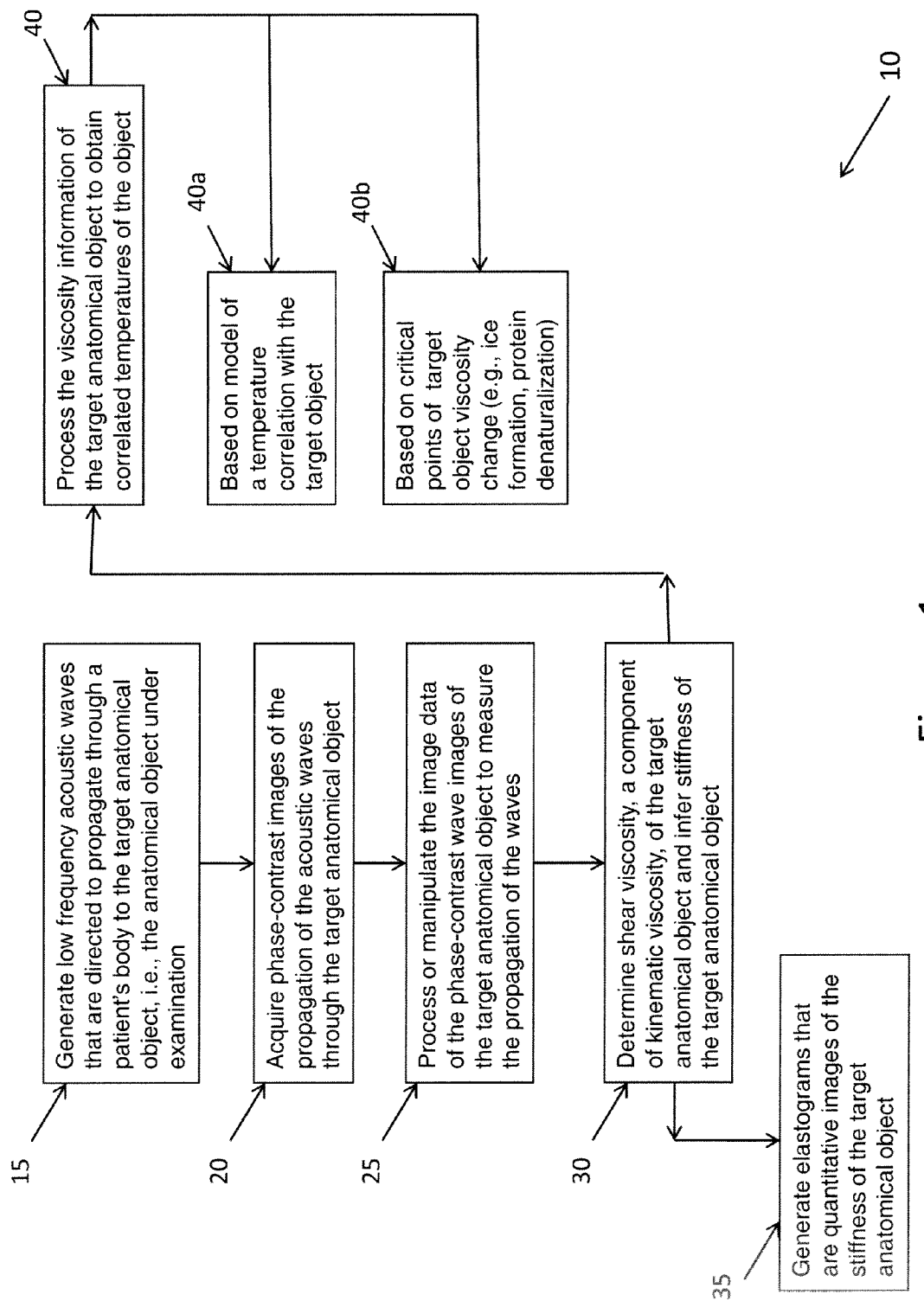
FIG. 1 is a flow chart of an MR elastography-based method carried out in accordance with the present invention.

FIG. 1 shows a flow chart of the MR elastography-based method 10 carried out in accordance with the present invention. In the method 10, an external wave generator or acoustic transducer generates low frequency acoustic waves that are directed to propagate through a patient's body and through the target anatomical object, i.e., the anatomical object under examination, or a region of interest (Step 15). The acoustic waves may be oscillatory (sinusoidal) shear waves of a given low frequency, for example, in the range of 20-65 Hz. Also, the acoustic waves may be applied in pulses having a cycle time that takes into account TE (echo delay) of the MR imaging, for example, 20 ms.

The propagation of mechanical waves through a target anatomical object may be used to reveal the relative stiffness of the anatomic structures. The method 10 employs an MR imaging system using phase-contrast gradient-echo sequences at different phase offsets to acquire images of the propagation of the acoustic waves through the target anatomical object (Step 20). Generally, to acquire phase-contrast (or phase-difference) wave images, the MR imaging system adds two opposing gradient pulses to the imaging sequence of pulses. In image pixels containing a static target object, the effects of the two pulses cancel, but if the target object moves in the time between the pulses, a phase shift appears in that pixel proportional to velocity along the gradient's direction. The MR imaging system then constructs a phase-contrast image by taking the difference between two scans, a reference scan and a velocity-encoded scan, which removes any uncontrolled phase errors.

The MR imaging system scanner further processes or manipulates the image data of the phase-contrast wave images of the target object to measure the propagation of the waves and infer shear stiffness of the target object (this is more fully described in an article by O. Rouviere, M. Yin, M. A. Dresner, et. al., entitled "MR Elastography of the Liver: Preliminary Results," Radiology, vol. 240, no. 2, August 2006, which is incorporated by reference herein) (Step 25). When measurements are obtained at multiple frequencies of the propagating waves, it is possible to determine shear viscosity, a component of kinematic viscosity (this is more fully described in an article by S. A. Kruse, J. A. Smith, A. J. Lawrence, et. al., entitled "Tissue Characterization using Magnetic Resonance Elastography: preliminary results," Phys. Med. Biol. 2000; 45:1579-1590, which is incorporated by reference herein) (Step 30). Generally, the wave propagation speed and the damping of acoustic waves in anatomical objects changes with the driving frequency due to the dispersion of the waves in the object. A characterization of the viscoelastic properties of the anatomical object is achieved by processing the MR acquisition of the propagating waves. The relative stiffness of the anatomic structures is on the order of nanometers.

Figure 3:
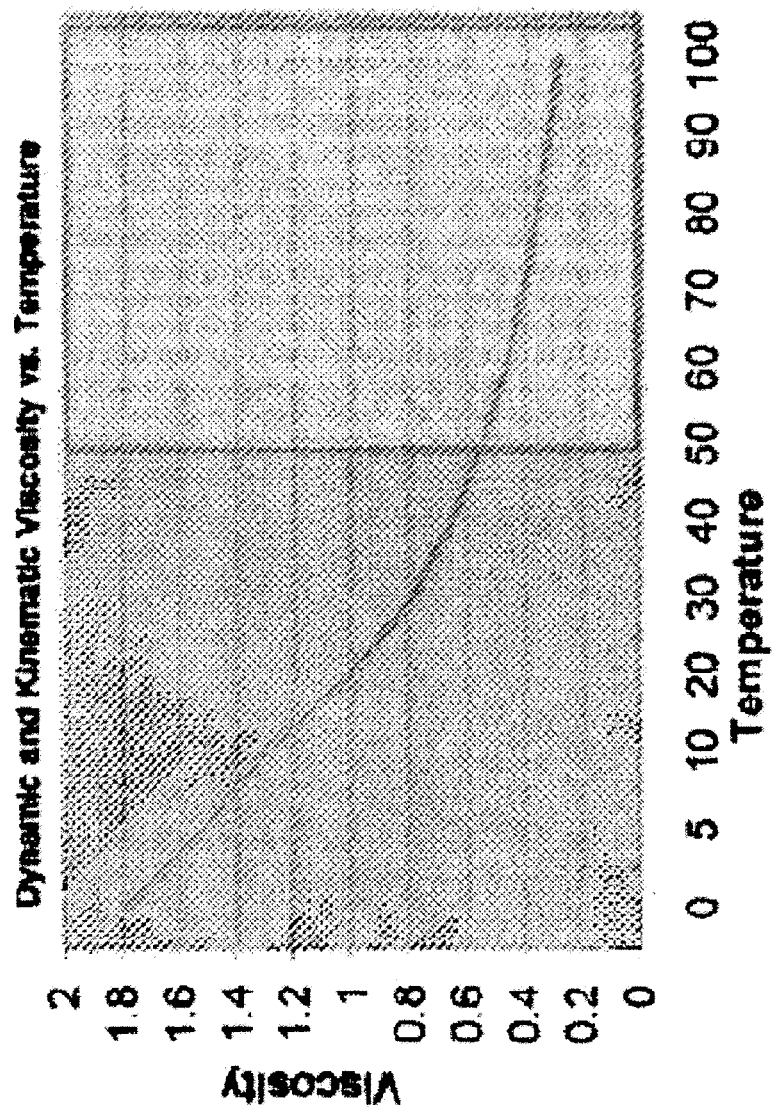
FIG. 3 is a plot of dynamic and kinematic viscosity versus temperature (in ° C.) for water.

From the above processing of the wave images, the MR imaging system may generate elastograms that are quantitative images of object stiffness (Step 35). Such elastograms may be used by health professionals to visualize and assess the condition of the target anatomical object. Thus, the MR imaging system enables the visualization of mechanical properties (i.e., viscosity) of the target anatomical object by imaging motion-encoded shear waves propagating through the object The MR imaging system processes the viscosity information of the target anatomical object to obtain correlated temperatures of the object (Step 40). Generally, viscosity of a material varies or correlates with temperature of a material. The case of water is illustrated in FIGS. 2 and 3, which are a table showing the values of dynamic viscosity and kinematic viscosity of water at different temperatures (in ° C.) and a plot of dynamic and kinematic viscosity versus temperature (in ° C.) for water, respectively. In order to obtain a similar correlation for the target anatomical object, a temperature correlation with the target object must be modeled (Step 40*a*). In the case of tissue, although the method 10 may use a generalized tissue model, each of the multiple tissue types (e.g., bone, liver, etc.) should be modeled to obtain a more accurate temperature correlation. The method 10 may use masks taken from anatomical images to define regions of the different tissue types. Once these masks are defined, they dictate the tissue model to be used in each region. The mask and corresponding tissue model can then determine the temperature when the given elastography information is given. The masks may be defined manually, semi-automatically, or fully automatically via existing segmentation approaches, such as, region growing, level-sets, random walker, etc.

As shown in FIG. 2, both the dynamic viscosity and the kinematic viscosity of water vary with temperature. It is noted, though, that it is difficult to model and determine the exact temperature correlation with a specific tissue type. However, the method 10 may achieve a satisfactory temperature estimation of particular applications (Step 40*b*). For example, as an alternative, the method 10 may determine viscosity changes indicative of an increase in temperatures. As tissue is heated, the viscosity changes are different than that of water. In particular, tissue will have higher viscosities than that of water but will have severe drops in viscosity values after about 50° C. due to rapid protein denaturalization (this is more fully described in an article by S. H. Wong, R. D. Watkins, M. Kupnik, K. B. Pauly, and B. T. Khuri-Yakub, entitled "Feasibility of MR-Temperature Mapping of Ultrasonic Heating from a CMUT", IEEE Trans. on Ultrasonics, Ferroelectrics, and Frequency Control, vol. 55, No. 4, April 2008, which is incorporated by reference herein). Such a change can be easily detected by an elasticity measurement. Unlike in MR imaging techniques using proton resonance frequency shift, no baseline is necessary nor is a region without anticipated temperature changes necessary.

Further, the MR imaging system may detect the formation of ice (and thereby estimate temperature) on regions of the target anatomical object (resulting, for example, from a cryoablation procedure), by analyzing the propagating waves around the regions of the target object and nearby objects. The formation of ice causes a sudden increase in viscosity but the existence of ice on regions of the target object creates imaging artifacts and no readings can be obtained directly. But the MR imaging system assumes a region that causes a rapid progression of propagating waves is dense and may detect its focal point by the direction of the propagating waves. In this way, the MR imaging system may then provide an estimation of the temperatures of regions of the target object.

Figure 4:
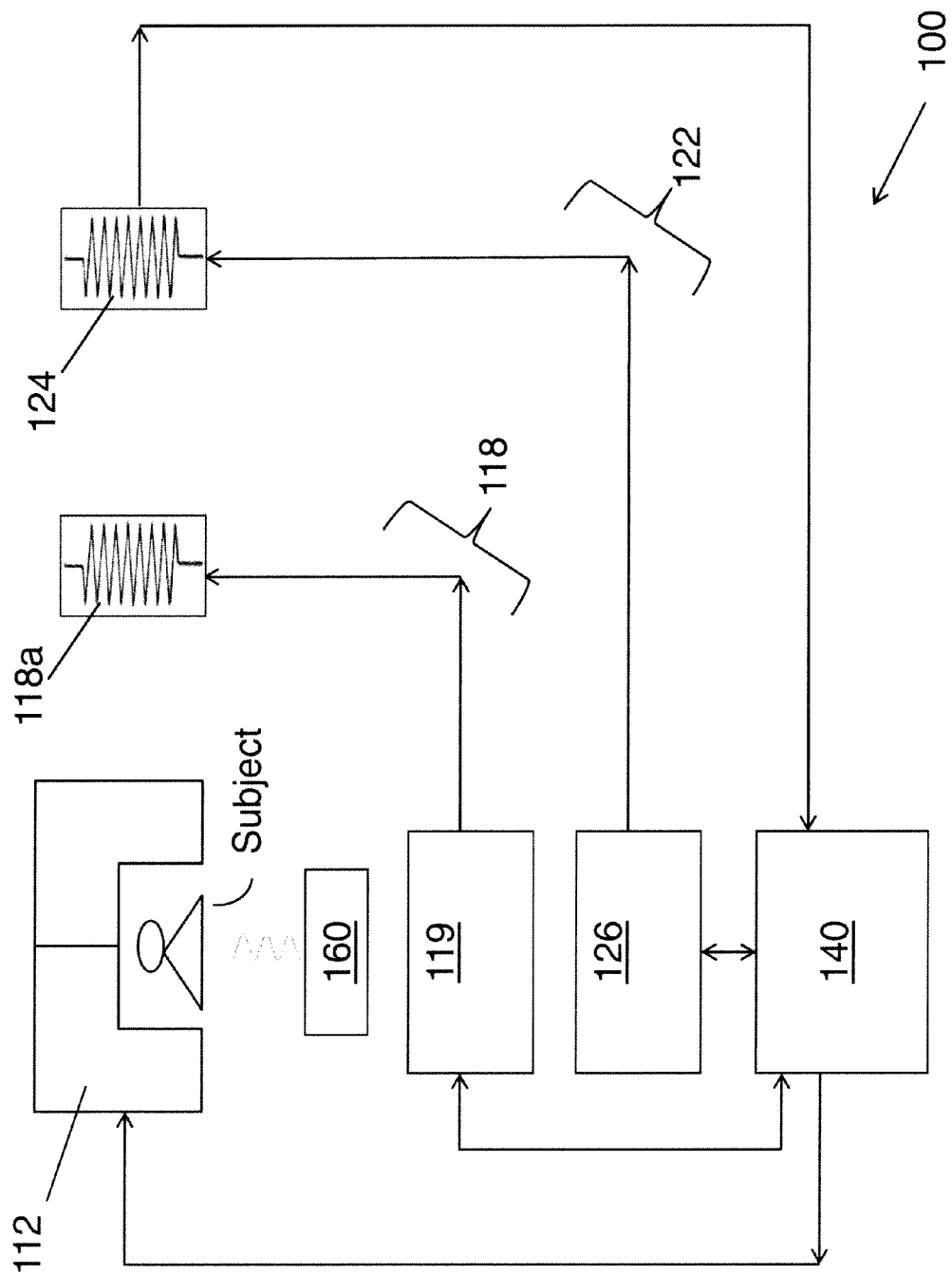
FIG. 4 is a block diagram of an MR imaging system (simplified) that may implement the method of FIG. 1.

FIG. 4 is a block diagram of a conventional MR imaging system 100 (simplified) that may perform the method 10 in accordance with the present invention. A main magnet 112 generates a strong static magnetic field in an imaging region where the subject (i.e., patient) is introduced. The magnet 112 is used to polarize the target anatomical object, i.e., certain atoms in the target anatomical object that were previously randomly-ordered become aligned along the magnetic field. A gradient coil system 118, having a gradient coil subsystem 118*a* and a gradient coil control unit 119, generates a time-varying linear magnetic field gradient in respective spatial directions, x, y and z, and spatially encodes the positions of the polarized or excited atoms. An RF system 122, having an RF coil subsystem 124 and a pulse generation unit 126, transmits a series of RF pulses to the target anatomical object to excite the "ordered" atoms of the target anatomical object. The RF coil subsystem 124 may be adapted to switch between a transmission mode and receiver mode.

A control or computer system 140 coordinates the pulse generation unit 126, the gradient coil control unit 119, and other components to carry out a desired MR image pulse sequence. As noted above, the method 10 may use a phase-contrast gradient-echo MR image pulse sequence. The MR imaging system 100 repeats the MR image pulse sequence a number of times so the atoms oscillate around the polarized alignment direction (along the main magnetic field) during the excited state caused by the energy of RF pulses. The atoms release the RF energy, i.e., generate an RF signal, during the resonance or oscillation and as the atoms return to their respective alignments. The RF coil subsystem 124 receives or detects the released RF energy and generates spatially-coded MR signals to the computer system 140. It is noted that the subject may be injected with contrast agent that permeates the target anatomical object in order to assist in the capture of image data and the resulting image visualization.

The MR imaging system 100 works in combination with an external wave generator (or acoustic transducer, ultrasound transducer, etc.) 160 that generates low frequency acoustic waves (i.e., oscillatory shear stress waves) directed to propagate through the patient's body and through the target anatomical object or a region of interest. It is noted that the method 10 is described above using a given frequency to measure stiffness or viscosity although multifrequency MR elastography may also be used. It is further noted that, during ablation, a low-frequency vibration is necessary for the elastography measurements. This may interfere with the health professional in cases of intervention. However, the measurements are only necessary when the ablation probe is in place. Additionally, the vibration follows a predictable pattern which the health professional can take into account. Given HIFU therapy, an ultrasound transducer is already present and may be used as a transducer source for elastography measurements.

The MR imaging system 100 images the waves propagating through the target anatomical object using the above described MR method 10. In brief, the system 100 images the propagation caused by the introduced shear waves by applying motion-sensitive gradients. The computer system 140, which controls the operation of the MR imaging system 100 and its components, processes the MR signals to transform them into image data of the target anatomical object (i.e., reconstructed MR images) for display, storage, and/or other usage. The MR imaging system 100 and, in particular, the computer system 140, is adapted to permit the imaging system 100 to operate and to implement methods of the present invention, for example, as shown in FIG. 1. More particularly, the computer system 140 manipulates the image data as described above to measure the target anatomical object viscosity and to obtain a temperature mapping of the target anatomical object. From the above processing of the wave images, the MR imaging system 100 may then generate appropriate visualizations of the temperature mapping of the target anatomical object for use by health professionals.

The method 10 provided by the present invention does not require base-line images and does not need to account for drifts to perform MR temperature mapping. The method 10 makes use of MR elastography to determine the density of a target anatomical object which is then correlated to temperature when assuming a specific anatomical object model. In the cases where the precision at which temperatures can be determined is uncertain, the method 10 may detect critical points of anatomical object change (and, thus, changes in viscosity), such as ice formation and protein denaturalization, to provide temperature estimations.

Advantageously, existing MR elastography protocols, such as in the liver, can employ the method 10 with little or no change to afford temperature mapping as additional data. Further, the method 10 may be performed (typical time of 15 seconds) at the end of a standard MR imaging of the target anatomical object (typical time of 45 minutes for a liver scan).

Other modifications are possible within the scope of the invention. For example, although the steps of the method 10 have been described in a specific sequence, the order of the steps may be re-ordered in part or in whole and the steps may be modified, supplemented, or omitted as appropriate. Also, the method 10 may use various well known algorithms and software applications to implement the steps and substeps. Further, the method 10 may be implemented in a variety of algorithms and software applications. Further, the method 10 may be supplemented by additional steps or techniques.

The invention claimed is:

1. A method of acquiring temperature measurements from inside an anatomical object during a medical procedure using magnetic resonance (MR) elastography, comprising:

(a) segmenting an image of the anatomical object to define a region for each different tissue type comprising the anatomical object;

(b) obtaining a measurement of viscosity of a respective defined region of the anatomical object using the MR elastography;

(c) correlating the viscosity measurement to a respective temperature of the anatomical object utilizing a respective model of viscosity at different temperatures for the respective defined region;

(d) obtaining a temperature measurement in real-time from the correlation of the viscosity measurement to the respective temperature to generate a temperature mapping of the anatomical object; and (e) generating and displaying a visualization of the temperature mapping to determine temperature changes for the medical procedure, and wherein steps (a), (b), (c), (d) and (e) are performed by a computer.

2. The method of claim 1, wherein the segmenting step comprises masking the image of the anatomical object to delineate a respective region.

3. The method of claim 1, wherein the respective model of viscosity at different temperatures for the defined region comprises a generalized model of tissue viscosity at different temperatures.

\* \* \* \* \*